US012539429B2

(12) United States Patent
Meskens

(10) Patent No.: US 12,539,429 B2
(45) Date of Patent: *Feb. 3, 2026

(54) AUTONOMOUS IMPLANTABLE MEDICAL DEVICE TUNING

(71) Applicant: Cochlear Limited, Macquarie University (AU)

(72) Inventor: Werner Meskens, Mechelen (BE)

(73) Assignee: Cochlear Limited, Macquarie University (AU)

( * ) Notice: Subject to any disclaimer, the term of this patent is extended or adjusted under 35 U.S.C. 154(b) by 1094 days.

This patent is subject to a terminal disclaimer.

(21) Appl. No.: 17/091,047

(22) Filed: Nov. 6, 2020

(65) Prior Publication Data

US 2021/0060347 A1 Mar. 4, 2021

Related U.S. Application Data

(63) Continuation of application No. 15/465,678, filed on Mar. 22, 2017, now Pat. No. 10,864,379.

(51) Int. Cl.
*A61N 1/378* (2006.01)
*A61N 1/36* (2006.01)
*A61N 1/372* (2006.01)

(52) U.S. Cl.
CPC ....... *A61N 1/3787* (2013.01); *A61N 1/36036* (2017.08); *A61N 1/37252* (2013.01)

(58) Field of Classification Search
CPC . A61N 1/3752; A61N 1/36036; A61N 1/3787
See application file for complete search history.

(56) References Cited

U.S. PATENT DOCUMENTS

| | | | | |
|---|---|---|---|---|
| 8,369,959 | B2 | 2/2013 | Meskens | |
| 8,538,545 | B2 | 9/2013 | Meskens | |
| 8,953,810 | B2 | 2/2015 | Meskens et al. | |
| 9,707,406 | B1 * | 7/2017 | Dellamano | H02J 50/40 |
| 10,864,379 | B2 * | 12/2020 | Meskens | A61N 1/3787 |
| 2005/0131495 | A1 * | 6/2005 | Parramon | A61N 1/3787 607/33 |
| 2012/0004708 | A1 | 1/2012 | Chen | |
| 2012/0109256 | A1 | 5/2012 | Meskins et al. | |

(Continued)

*Primary Examiner* — Jennifer Pitrak McDonald
*Assistant Examiner* — Jennifer Ghand
(74) *Attorney, Agent, or Firm* — Edell, Shapiro & Finnan, LLC

(57) ABSTRACT

Presented herein are implantable medical devices that comprise an implantable portion having a resonant tank circuit that is used to receive signals from one or more external devices. The resonant tank circuit is configured to operate at first and second resonant frequencies, where the first resonant frequency is optimized to exchange data with, and potentially receive operating power from, an external device, while the second resonant frequency is optimized to receive charging power. In certain embodiments, upon initiating operation of the implantable portion with at least one external device, the implantable portion is configured to force tune the resonant tank circuit to the first resonant frequency. That is, when the resonant tank circuit first begins receiving signals from an external device, the signals received at the resonant tank circuit are used to initially tune the resonant tank circuit to the first resonant frequency.

20 Claims, 6 Drawing Sheets

(56) References Cited

U.S. PATENT DOCUMENTS

| | | | | |
|---|---|---|---|---|
| 2012/0274270 | A1 | 11/2012 | Dinsmoor | |
| 2013/0103115 | A1 * | 4/2013 | Dronov | H04Q 9/12 607/60 |
| 2014/0058479 | A1 | 2/2014 | Rahman | |
| 2015/0209591 | A1 | 7/2015 | Meskens | |
| 2015/0343225 | A1 | 12/2015 | Leigh | |
| 2022/0072306 | A1 * | 3/2022 | Bennett | A61N 1/37223 |

* cited by examiner

690

AUTONOMOUS IMPLANTABLE MEDICAL DEVICE TUNING

CROSS-REFERENCE TO PREVIOUS APPLICATIONS

This application is a continuation of U.S. application Ser. No. 15/465,678, filed on Mar. 22, 2017, entitled "Autonomous Implantable Medical Device Tuning," the contents of which are hereby incorporated by reference in their entirety.

BACKGROUND

Field of the Invention

The present invention relates generally to implantable medical devices.

Related Art

Medical devices having one or more implantable components, generally referred to herein as implantable medical devices, have provided a wide range of therapeutic benefits to recipients over recent decades. In particular, partially or fully-implantable medical devices such as hearing prostheses (e.g., bone conduction devices, mechanical stimulators, cochlear implants, etc.), implantable pacemakers, defibrillators, functional electrical stimulation devices, and other implantable medical devices, have been successful in performing lifesaving and/or lifestyle enhancement functions for a number of years.

The types of implantable medical devices and the ranges of functions performed thereby have increased over the years. For example, many implantable medical devices now often include one or more instruments, apparatus, sensors, processors, controllers or other functional mechanical or electrical components that are permanently or temporarily implanted in a recipient. These functional devices are typically used to diagnose, prevent, monitor, treat, or manage a disease/injury or symptom thereof, or to investigate, replace or modify the anatomy or a physiological process. Many of these functional devices utilize power and/or data received from external devices that are part of, or operate in conjunction with, the implantable medical device.

SUMMARY

In one aspect an implantable portion of a hearing prosthesis is provided. The implantable portion comprises: a rechargeable battery; and an implantable resonant tank circuit including an implantable coil, wherein the implantable portion of the hearing prosthesis is configured to tune the resonant tank circuit to, alternatively, resonate at first and second frequencies: wherein the implantable portion of the hearing prosthesis tunes the resonant tank circuit to resonate at the second frequency to receive charging power, via the implantable coil, when recharging the battery, and wherein the implantable portion of the hearing prosthesis tunes the resonant circuit to resonate at the first frequency to exchange data with a first external device, via the implantable coil, when not recharging the battery, and wherein the first frequency is substantially different from the second frequency In another aspect an implantable medical device is provided. The implantable medical device comprises: a resonant tank circuit including an implantable coil, wherein the resonant tank circuit is configured to operate at first and second resonant frequencies; and at least one radio frequency tuning switch that is selectively actuated to switch a resonant frequency of the resonant tank circuit between the first and second resonant frequencies, wherein the at least one radio frequency tuning switch is configured to force tune the resonant tank circuit to the first resonant frequency upon initiation of the implantable medical device, wherein the first resonant frequency is optimized to concurrently receive operating power and data at the implantable coil, and wherein the second resonant frequency is optimized to receive charging power at the implantable coil.

In another aspect a method is provided. The method comprises: initiating operation of an implantable portion of a hearing prosthesis with at least one external device via an inductive link; receiving, via the inductive link, radio frequency signals at a resonant tank circuit of the implantable portion of the hearing prosthesis; in response to receipt of the radio frequency signals, initially forcing the implantable resonant tank circuit to a first state with a first resonant frequency; and with an implant controller in the implantable portion, overriding the first state to tune the resonant tank to a second resonant frequency.

BRIEF DESCRIPTION OF THE DRAWINGS

Embodiments of the present invention are described herein in conjunction with the accompanying drawings, in which.

DETAILED DESCRIPTION

Embodiments presented herein are generally directed to implantable medical devices that comprise an implantable portion having a resonant tank circuit that is used to receive signals from one or more external devices. The resonant tank circuit is configured to switch between first and second resonant frequencies, where the first resonant frequency is optimized to exchange data with, and potentially receive operating power from, an external device, while the second resonant frequency is optimized to receive charging power. In certain embodiments, upon initiating operation of the implantable portion with at least one external device, the implantable portion is configured to force tune the resonant tank circuit to the first resonant frequency. That is, when the resonant tank circuit first begins receiving signals from an external device, the signals received at the resonant tank circuit are used to initially tune the resonant tank circuit to the first resonant frequency. Subsequently, the implantable portion can tune the resonant tank circuit to the second resonant frequency.

There are a number of different types of implantable medical devices in which embodiments of the present invention may be implemented. However, merely for ease of illustration, the techniques presented herein are primarily described with reference to one type of implantable medical device, namely a cochlear implant. It is to be appreciated that the techniques presented herein may be used in any other partially or fully implantable medical device now known or later developed, including other auditory prostheses, such as auditory brainstem stimulators, electro-acoustic hearing prostheses, bimodal hearing prostheses, etc.

Figure 1:
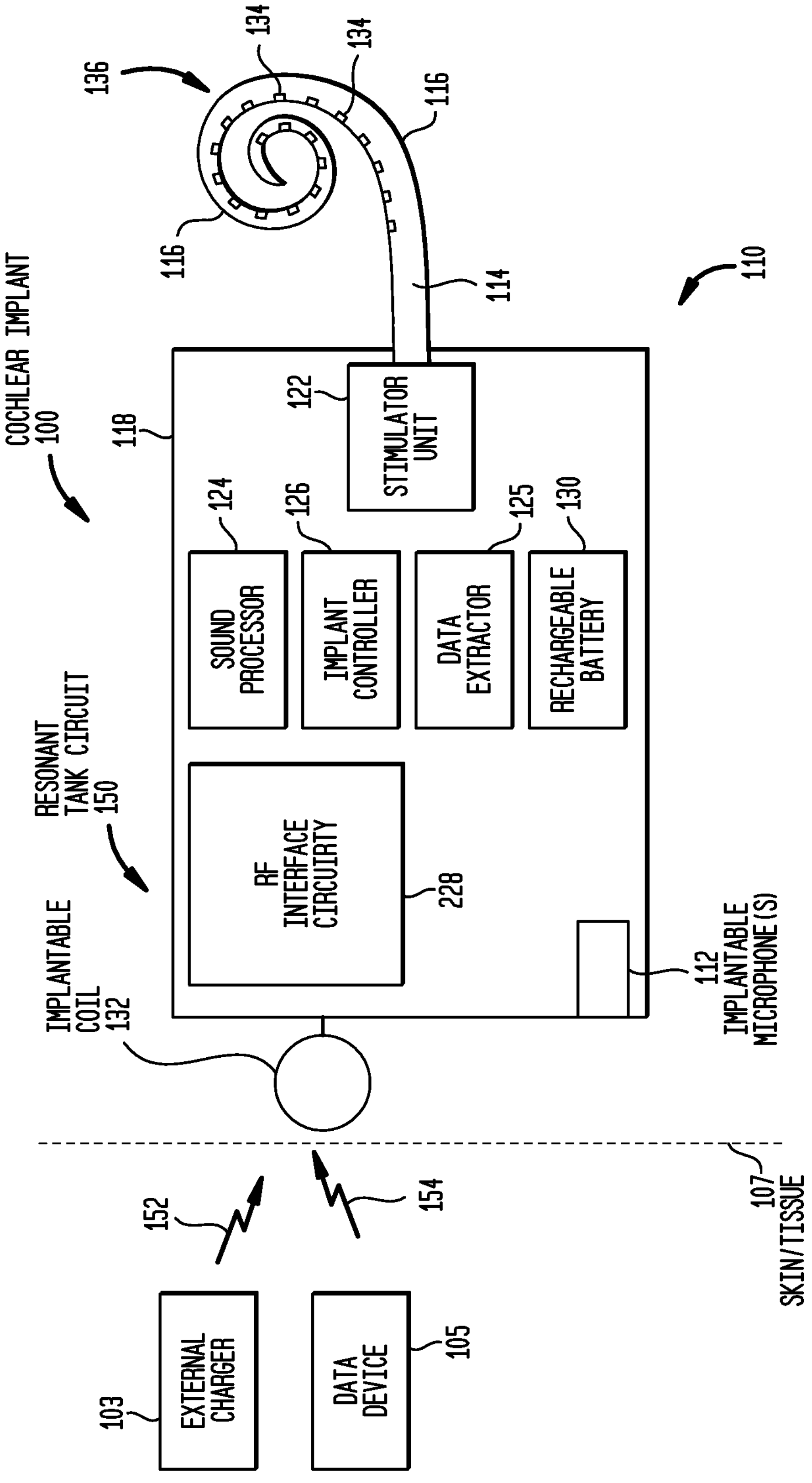
FIG. 1 is a block diagram illustrating a cochlear implant system, in accordance with embodiments presented herein.

FIG. 1 is block diagram of an exemplary cochlear implant system 101 in which embodiments presented herein are implemented. The cochlear implant system 101 comprises a cochlear implant 100, an external charging device (external charger) 103, and an external data device 105. In the example arrangement of FIG. 1, cochlear implant 100 is a totally implantable cochlear implant where all components of the cochlear implant are configured to be implanted under the skin/tissue 107 of a recipient. Because all components are implantable, cochlear implant 100 operates, for at least a finite period of time, without the presence of any external devices/components, such as external charger 103 and/or external data device 105.

Cochlear implant 100 includes an implant body (main module) 110, a lead region 114, and an elongate intra-cochlear stimulating assembly 116. The implant body 110 generally comprises a hermetically-sealed housing 118 in which a stimulator unit (stimulation electronics) 122, one or more processors, such as a sound processor 124 and a data extractor component or data processor 125, an implant controller 126 (i.e., battery and power management component or battery processor), implant radio frequency (RF) interface circuitry 128, one or more implantable microphones 112, and a rechargeable battery 130 are disposed.

The implant body 110 also includes an internal/implantable coil 132 that is located external to the housing 118 and implant RF interface circuitry 128. A resonant tank circuit 150 is formed by the implantable coil 132 and one or more elements of the implant RF interface circuitry 128. The implantable coil 132 is connected to the implant RF interface circuitry 128 within the housing 118 via a hermetic feedthrough (not shown in FIG. 1). Implantable coil 132 is typically a wire antenna coil comprised of multiple turns of electrically insulated single-strand or multi-strand platinum or gold wire. The electrical insulation of implantable coil 132 is provided by a flexible molding (e.g., silicone molding), which is not shown in FIG. 1. Generally, a permanent magnet is fixed relative to the implantable coil 132. The permanent magnet helps to retain and align an external component by interacting with another magnet in an external device.

Elongate stimulating assembly 116 is configured to be at least partially implanted in the recipient's cochlea (not shown) and includes a plurality of longitudinally spaced intra-cochlear electrical stimulating contacts (electrodes) 134 that collectively form a contact array 136 for delivery of electrical stimulation (current) to the recipient's cochlea. Stimulating assembly 116 extends through an opening in the cochlea (e.g., cochleostomy, the round window, etc.) and has a proximal end connected to the stimulator unit 122 via the lead region 114 and a hermetic feedthrough (not shown in FIG. 1). Lead region 114 includes one or more conductors (wires) that electrically couple the electrodes 134 to the stimulator unit 122.

The one or more implantable microphones 112 are configured to detect/receive input sound signals that are provided to the sound processor 124. The sound processor 112 is configured to execute sound processing and coding to convert the received sound signals into output signals for use by the stimulator unit 122 in delivering electrical stimulation (current) to the recipient via electrodes 134. In this way, cochlear implant 100 electrically stimulates the recipient's auditory nerve cells, bypassing absent or defective hair cells that normally transduce acoustic vibrations into neural activity, in a manner that causes the recipient to perceive one or more components of the received sound signals.

Although cochlear implant 100 is totally implantable and able to operate without the presence of any external devices, there are times when the presence of one or more external devices are needed. As such, in the example of FIG. 1, the external charger 103 and the data device 105 may operate with the cochlear implant 100 during different times. In general, the external charger 103 is configured to deliver charging power to the cochlear implant 100 via an inductive link 152, while the data device 105 is configured to exchange data with, and potentially send operating power to, the cochlear implant via an inductive link 154. The signals exchanged over inductive links 154 and 152 are radio frequency signals (i.e., electric currents that oscillate at radio frequencies) that are sent using first and second frequencies, respectively. That is, as described further below, the inductive link 152 operates at a first frequency, while the inductive link 154 operates a second frequency that is different than the first frequency.

The external charger 103 and the data device 105 may each have a number of different forms. For example, the external charger 103 may comprise a headpiece coil wired to a battery pack, a headpiece power charger in the shape of a button, a charging headband, a pillow charger, etc. The data device 105 may comprise, for example, a behind-the-ear (BTE) processor, an off-the-ear headpiece (i.e., a button processor), etc.

As noted above, the cochlear implant 100 comprises the resonant tank circuit 150 that includes the implantable coil 132 and one or more elements of the implant RF interface circuitry 128. The resonant tank circuit 150 is used, at different times, to receive the charging power from the external charger 103 and to exchange data with, and potentially receive operating power from, the data device 105. As noted, the transfer of the charging power to the cochlear implant 100 occurs using a frequency that is different from the frequency used for the exchange of data and/or transfer of operating power (i.e., inductive links 152 and 154 operate at different frequencies). As such, to improve transfer/link efficiency during operation of each of the inductive links 152 and 154, the resonant tank circuit 150 is configured to switch between at least two different resonant frequencies, namely a first resonant frequency that is optimized for exchange the data with, and/or receive operating power from, the data device 105 (i.e., a resonant frequency that substantially matches the frequency at which the data and/or operating power is transmitted) and a second resonant frequency that is optimized to receive the charging power from the external charger 103 (i.e., a resonant frequency that substantially matches the frequency at which the charging operating power is transmitted).

The resonant tank circuit 150 includes an adjustable resonant configuration that enables the selection of the two different resonant/tuning frequencies (i.e., a frequency shift option). For ease of illustration, certain embodiments presented herein will be primarily described with reference to a resonant tank circuit that can be switched between a resonant frequency of approximately 5 Megahertz (MHz)

and a resonant frequency of approximately 6.78 MHz, while other embodiments presented herein are primarily described with reference to a resonant tank circuit that can be switched between a resonant frequency of approximately 15 MHz and a resonant frequency of approximately 13.56 MHz. However, it is to be appreciated that these specific resonant frequencies are illustrative and that the techniques presented herein may be used with other circuitry having different resonant frequencies. For example, to receive charging power, resonant tank circuits in accordance with embodiments presented herein may be configured to have resonant frequencies that reside in any of a number of industrial, scientific and medical (ISM) radio bands, such as in a 6.765 MHz to 6.795 MHz band (having a center frequency of 6.78 MHz), in the 13.553 MHz to 13.567 MHz band (having a center frequency of 13.56 MHz), in the 26.957 MHz to 27.283 MHz band (having a center frequency of 27.12 MHz), etc.

In the illustrative examples in which the resonant tank circuit 150 can be switched between 5 MHz and 6.78 MHz, the 5 MHz resonant frequency supports a combined power and data transfer, where the data transfer may be bi-directional. The operating power and data can be modulated with one another (e.g., using on-off-keying (OOK)) or separated from one another and interleaved (e.g., time division multiple access (TDMA)). The 6.78 MHz resonant frequency is utilized only for the purpose of transferring the charging power from the external charger 103 (or another external charging device) to cochlear implant 100 during recharge operations (i.e., the 6.78 MHz frequency is used to receive power that can recharge the battery 130). More specifically, when the implantable coil 132 is coupled with external charger 103 (i.e., when the implantable coil 132 and a coil within the external charger 103 are located in proximity to one another to form an inductive coupling), the external charger 103 generates a magnetic field that oscillates at approximately 6.78 MHz, which in turn induces current flow in the implantable coil 132. The implantable coil 132 is part of the resonant tank circuit 150, which can use the current induced in the implantable coil 132 to charge the rechargeable battery 130.

In general, the operating power received at 5 MHz enables real-time operation of the cochlear implant 100, but is insufficient in magnitude/amplitude to charge battery 130. However, the charging power has an amplitude that is substantially higher than that of the operating power and, as such, is sufficient to recharge the battery 130. In certain examples, the charging power has emanates from magnetic field signals that have a magnitude that is at least five times larger, and in certain embodiments at least ten times larger, than the magnitude of the magnetic field signals comprising the operating power.

In addition to the alternative operation of the resonant tank circuit 150 at the first or second resonant frequency, the cochlear implant 100 is also configured such that when the cochlear implant 100 initiates communication with an external device via an inductive link (i.e., when the resonant tank circuit 150 first begins receiving radio frequency signals at the implantable coil 132), the resonant tank circuit 150 is automatically initially tuned to the first resonant frequency. That is, upon initiation of an inductive link with an external device, the cochlear implant is configured to initially force the resonant tank circuit 150 to a first state/arrangement in which the resonant tank circuit is initially tuned to operate at a first resonant frequency that is optimized for data communication. At a subsequent time, the implant controller 126 may override the first state and adjust the resonant tank circuit 150 to a second state/arrangement in which the resonant tank circuit operates at a second resonant frequency that is optimized for battery charging.

Figure 2:
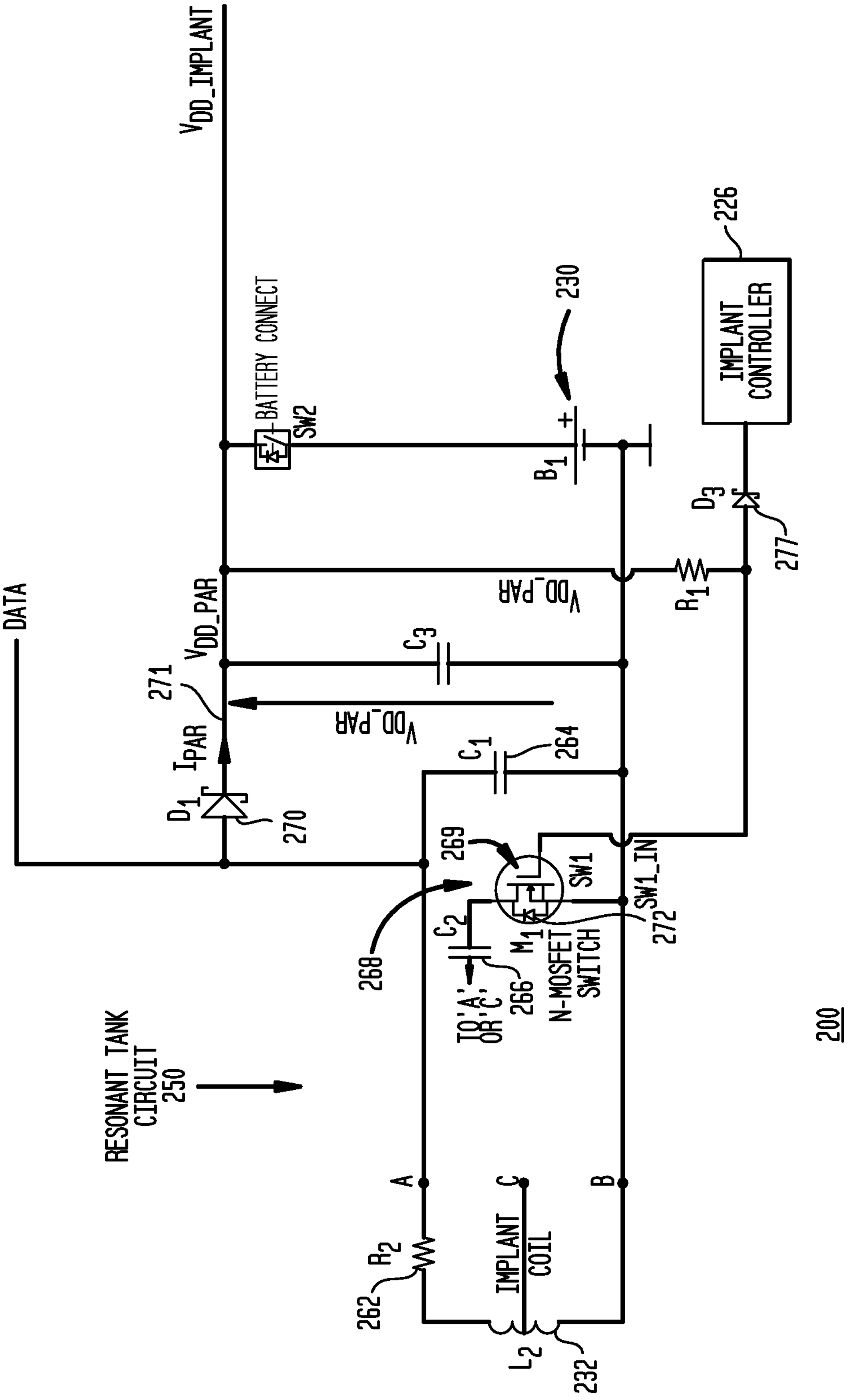
FIG. 2 is a schematic diagram illustrating a portion of a cochlear implant, in accordance with embodiments presented herein.

FIGS. 2, 3, 4, and 5 are schematic diagrams illustrating example arrangements for portions of an implantable medical device, such as cochlear implant 100, in accordance with embodiments presented herein. More specifically, referring first to FIG. 2, shown is a portion of a cochlear implant 200 that includes, among other elements, an implant controller 226, a rechargeable battery 230, an implant resonant tank circuit 250, and a radio frequency (RF) tuning switch 268. The resonant tank circuit 250 is formed by at least an implantable coil 232, which is represented in FIG. 2 by an inductor $L_2$, a resistor 262 (resistor $R_2$), a capacitor 264 (capacitor $C_1$), and, at certain times, a capacitor 266 (capacitor $C_2$). The capacitor 266 is connected between the implantable coil 232 (e.g., at points 'A' or 'C' in FIG. 2) and the RF tuning switch 268. In the example of FIG. 2, the RF tuning switch 268 is a metal-oxide-semiconductor field-effect transistor (MOSFET) and, more particularly, an N-channel MOSFET, sometimes referred to as a low-side switch.

The rechargeable battery 230 is configured to store the energy needed to power the other elements of the cochlear implant 200, as well as to provide the current needed to electrically stimulate the recipient's cochlea, for at least a period of time. As the cochlear implant 200 operates using the energy stored in the battery 230, the battery 230 is discharged and may need to be recharged by an external charging device (e.g., external charger 103).

The total amount of energy a rechargeable battery can store at any one time, often measured in terms of milliamp Hours (mAhs), is referred to herein as the maximum "capacity" of the battery. Rechargeable batteries, such as rechargeable battery 230, can only be safely charged to their associated maximum capacity and continuing to charge a rechargeable battery after the battery is fully charged can reduce the longevity of the battery itself and/or generate heat in the circuitry associated with the battery. In addition, under certain conditions the battery 230 may be disconnected. Implantable components such as cochlear implant 200 typically include Zener diodes, Tranzorbs, or other overvoltage protections that are designed to, once the implant battery is disconnected, protect the implant from overvoltage by dissipating part of the received RF energy as heat. Attempting to charge battery 230 after it is disconnected can damage these overvoltage protections and/or other elements of the cochlear implant 200.

For these and other reasons, the battery 230 is preferably only recharged when the cochlear implant 200 (e.g., implant controller 226) determines that there is a need to recharge the battery 230 (e.g., the implant controller 226 confirms that the battery is not already fully charged and/or the battery charge exceeds a predetermined threshold) and/or that the battery 230 is able to accept charging (e.g., confirm that the battery is not disconnected, battery end-of-life (EOL), etc.). As such, before charging operations begin, the cochlear implant 200 is configured to authorize an external charger to initiate the transmission of charging power to the cochlear implant through the use of a bidirectional data exchange.

Similar to the arrangement of FIG. 1, implantable coil 232 and the resonant tank circuit 250 are used for data communication with an external device (e.g., external data device 105), as well as for receiving charging power from an external charger (e.g., external charger 103). As such, the resonant tank circuit 250 is configured to operate at two distinct resonant frequencies, namely a first resonant frequency that is optimized for data communications (i.e., a resonant frequency that substantially matches the data transfer frequency) and a second frequency that is optimized for receipt of charging power (i.e., a resonant frequency that substantially matches the frequency used for transferring charging power). In the specific arrangements of FIG. 2, the first resonant frequency is lower than the second frequency. For example, the first frequency may be approximately 5 MHz and the second frequency may be approximately 6.78 MHz.

Since the implantable coil 232, and thus resonant tank circuit 250 are used for both data communication and for receiving charging power, problems could arise if the resonant tank circuit 250 operates at an improper resonant frequency. For example, if the resonant tank circuit 250 is unintentionally tuned to 6.78 MHz, the cochlear implant 200 may be unable to authorize the initiation of charging by an external charger, or conversely, prevent the initiation of charging by the external charger. This may be particularly problematic when the cochlear implant 200 is first initialized/started (i.e., when the cochlear implant 200 is first powered and the resonant tank circuit 250 begins to receive radio frequency signals from an external device) and, for various reasons, the implant controller 226 may be unable to adjust the resonant frequency of the resonant tank circuit 250 to 5 MHz. Therefore, in accordance with embodiments presented herein, the cochlear implant 200 is configured such that when the cochlear implant initiates operation with an external device via an inductive link, the resonant tank circuit 250 is automatically initially tuned to the first resonant frequency that is optimized for data communications (i.e., the resonant tank circuit 250 is always forced to begin operating at the first resonant frequency that is optimized for transfer of data and/or operating power). At a subsequent time, the resonant tank circuit 250 may be adjusted so as to shift the resonant frequency to a second resonant frequency that is optimized for transfer of charging power to the cochlear implant 200.

As noted above, the resonant tank circuit 250 includes the RF tuning switch 268. When the RF tuning switch 268 is open (i.e., non-conducting), only capacitor 264 is connected with the implantable coil 232 and the resonant frequency of the resonant tank circuit 250 is controlled by the inductance of the implantable coil 232 (i.e., the value of $L_2$) and the capacitance associated with capacitor 264. However, when the RF tuning switch 268 is closed, capacitor 266 is added into the resonant tank circuit 250 in parallel with capacitor 264 and the resonant frequency of the resonant tank circuit 250 is controlled by the inductance of the implantable coil 232 (i.e., the value of $L_2$) and the parallel capacitance associated with capacitors 264 and 266.

Therefore, in the example of FIG. 2, the resonant frequency of the resonant tank circuit 250 is controlled (i.e., shifted downward) by selectively opening/closing the RF tuning switch 268 to alter one or more of the inductive or capacitive part of the resonant circuit. When the RF tuning switch 268 is open, the resonant tank circuit 250 is optimized for receiving charging power (e.g., the resonant tank circuit resonates at approximately 6.78 MHz). When the RF tuning switch 268 is closed, the resonant tank circuit 250 is optimized for receiving data and/or operating power (e.g., the resonant tank circuit resonates at approximately 5 MHz).

When the cochlear implant 200 initiates operation with an external device via an inductive link, the RF tuning switch 268 is always forced closed (conducting) so that both capacitor 266 and capacitor 264 are connected in parallel with the implantable coil 232. As a result, the cochlear implant 200 is configured such that the resonant tank circuit 250 is initiated at a resonant frequency of 5 MHz (i.e., a resonant frequency that is optimized for receiving data and/or operating power).

The RF tuning switch 268 is a MOSFET, sometimes referred to as MOSFET $M_1$, and, as described further below, the RF tuning switch 268 is forced closed by driving the gate 269 of the MOSFET with an output generated from received radio frequency signals. In certain embodiments, such as that of FIG. 2, the output generated from received radio frequency signals is the rectified voltage of the resonant tank circuit 250.

More specifically, a current is induced in the implantable coil 232 when there is a magnetic field (H-field) crossing through the implantable coil. The induced current in the implantable coil 232 creates a resonant tank voltage that is rectified by a diode 270 (diode $D_1$). That is, the cochlear implant 200 includes a diode 270 that, in response to the induced current in the implantable coil 232, generates a rectified tank voltage at 271. This rectified tank voltage is shown in FIG. 2 as $V_{DD\_PAR}$, which is used to drive the RF tuning switch 268 (i.e., drive gate 268 of the MOSFET $M_1$). The RF tuning switch 268 is an inverter such that when there is a sufficiently high voltage at gate 269 (i.e., when $V_{DD\_PAR}$ exceeds a predetermined threshold), the RF tuning switch 268 will be closed. In operation, the RF tuning switch 268 is configured such that even a small H-field crossing through the implant coil will close the switch. That is, the predetermined threshold at which $V_{DD\_PAR}$ will close the switch occurs even when the implantable coil 232 receives small magnetic fields. Therefore, when the cochlear implant of FIG. 2 initiates operation, and when the implantable coil 232 detects substantially any magnetic field, the rectified tank voltage (i.e., the rectified voltage of resonant tank circuit 250) will cause the RF tuning switch 268 to automatically close and tune the resonant frequency of the resonant tank circuit 250 to a first resonant frequency that is optimized for receiving data and/or operating power. In one example, this first resonant frequency is approximately 5 MHz.

It is to be understood that MOSFET $M_1$ is configured to form a conducting path between the source 's' and drain 'd' terminals (i.e., the switch 268 is configured to close) when there is a minimum gate-to-source voltage differential ($V_{gs}$). As such, it is to be understood that the threshold voltage that causes RF tuning switch 268 to close is a voltage that creates the minimum gate-to-source voltage differential that is needed to create a conducting path between the source and drain terminals of MOSFET $M_1$.

In general, the resonant tank circuit 250 is automatically initially tuned to a resonant frequency that is optimized for data communications (e.g., 5 MHz) so as to ensure that the cochlear implant 200 has the ability to conduct a data exchange (e.g., bidirectional data communication) with an external data device (e.g., data device 105 of FIG. 1). In addition, the use of the rectified tank voltage, rather than a control component such as implant controller 226, as the mechanism to automatically the resonant tank circuit 250 to the first frequency eliminates the situation in which the implant controller 226 is unable to properly operate and/or actuate the switch. The implant controller 226 would be unable to close the tuning switch when, for example, little or no internal power is available (i.e., the battery voltage is too low, the battery is disconnected, the battery is end-of-life (EOL), etc.).

Since the resonant tank circuit 250 is automatically initially tuned to a resonant frequency that is optimized for data communications (e.g., 5 MHz), the cochlear implant is able to conduct bidirectional data communications with an external device that confirms whether or not charging of the battery 230 is authorized. As such, force tuning the resonant tank circuit 250 to the first frequency optimized for data communication (and potentially operating power transfer) is a safety mechanism that ensures that operation of an external recharger is first authenticated or disabled/blocked when, for example, the battery is fully charged or EOL.

If battery charging is authorized, then implant controller 226 can switch/adjust the tuning of the resonant tank circuit 250 to the second resonant frequency (e.g., 6.78 MHz) that is optimized for receipt of the charging power (e.g., 6.78 MHz) by opening the RF tuning switch 268 and, accordingly, disconnecting capacitor 266. Stated differently, once charging is desired, the implant controller 226 pulls/forces the gate 269 of the MOSFET $M_1$ to ground via a Schottky diode 277 (diode $D_3$), thereby causing the switch to open (i.e., become non-conducting).

As shown, the RF tuning switch 268 includes an intrinsic diode 272. When the RF tuning switch 268 is open, direct current (DC) is created over the plates of capacitor 266. However, due to the presence of the diode 272 in the RF tuning switch 268, once the DC is established capacitor 266 is essentially “floating” and no alternating current (AC) passes across the capacitor. That is, capacitor 266 will retain some charge, but it functions as an AC open. However, when the RF tuning switch 268 is closed (as described above), the DC on capacitor 266 is removed and alternating current (AC) passes.

As noted elsewhere herein, in certain arrangements, the 5 MHz resonant frequency supports a combined/modulated power data transfer (e.g., OOK) or a separated and interleaved power and data transfer (e.g., TDMA) between the cochlear implant 200 and the external device. That is, 5 MHz resonant frequency enables the bidirectional data communication link, while at this same enabling the active electronics of the implant, such as implant controller 226, to receive sufficient power so as to open the RF tuning switch 268 and adjust the resonant frequency of the resonant tank circuit 250.

FIG. 2 illustrates an arrangement in which the resonant frequency of the resonant tank circuit 250 is adjusted by selectively placing a capacitor in parallel with the implantable coil 232. It is to be appreciated that this technique for adjusting the resonant frequency of a resonant tank circuit is illustrative and that other techniques for adjusting the resonant frequency can be used in other embodiments presented herein. For example, FIG. 3 illustrates an alternative arrangement in which the resonant frequency of a resonant tank circuit is adjusted by selectively shorting a series capacitor.

Figure 3:
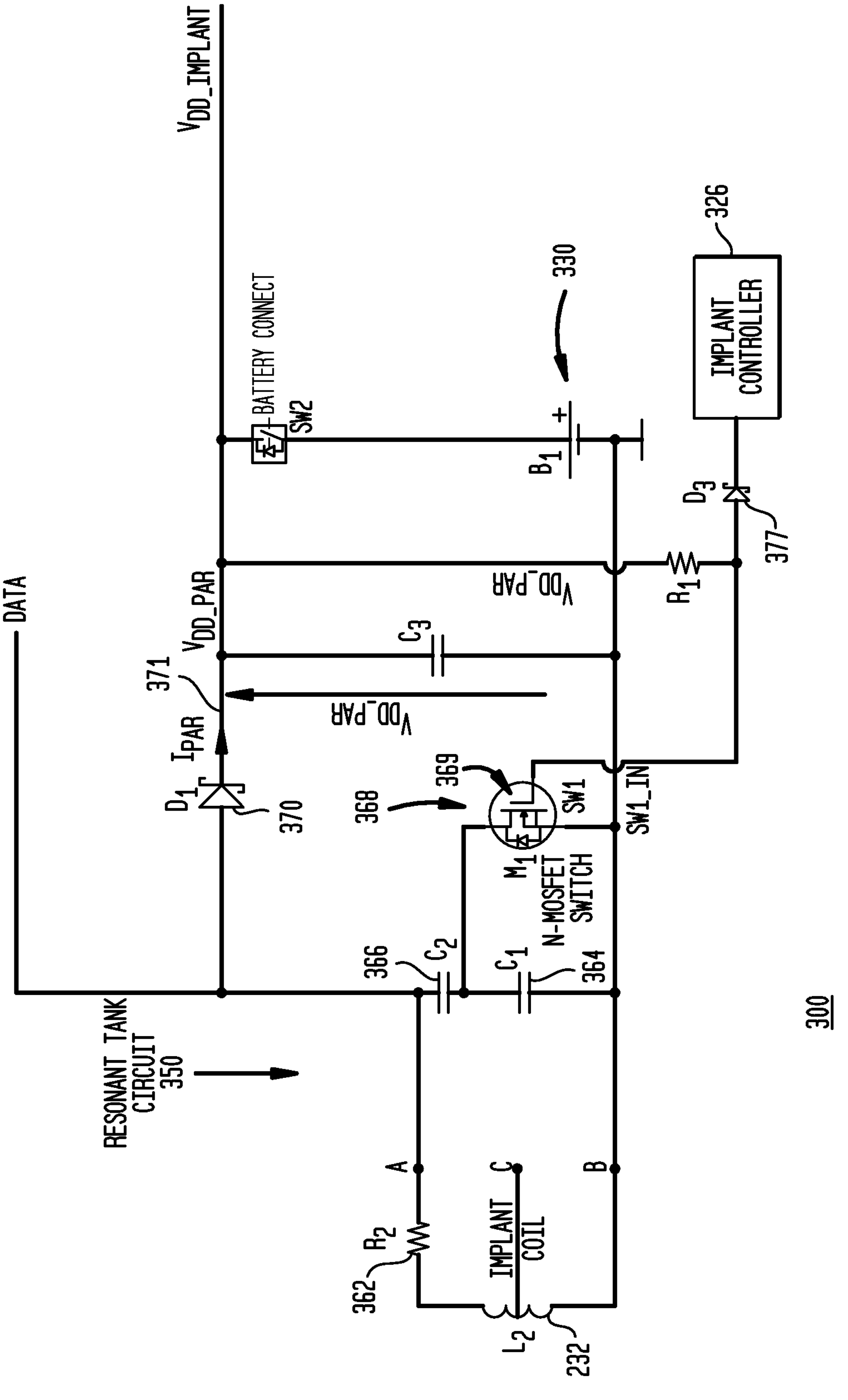
FIG. 3 is a schematic diagram illustrating a portion of a cochlear implant, in accordance with embodiments presented herein.

More specifically, FIG. 3 illustrates a portion of a cochlear implant 300 that includes, among other elements, an implant controller 326, a rechargeable battery 330, an implant resonant tank circuit 350, and an RF tuning switch 368. The resonant tank circuit 350 is formed by at least an implantable coil 332, which is represented in FIG. 3 by an inductor $L_2$, a resistor 362 (resistor $R_2$), a capacitor 366 (capacitor $C_2$), and, at certain times, a capacitor 364 (capacitor $C_1$). The capacitors 364 and 366 are connected in series with one another and an RF tuning switch 368 is connected in parallel with the capacitor 364. In the example of FIG. 3, the RF tuning switch 368 is an N-channel MOSFET.

The rechargeable battery 330 is configured to store the energy needed to power the other elements of the cochlear implant 300, as well as to provide the current needed to electrically stimulate the recipient’s cochlea, for at least a period of time. Similar to the arrangement of FIG. 2, the implantable coil 332 and the resonant tank circuit 350 are used for data communication with an external device (e.g., external data device 105), as well as for receiving charging power from an external charger (e.g., external charger 103). That is, the resonant tank circuit 350 is configured to operate at a first resonant frequency that is optimized for data communications (e.g., 5 MHz) and a second frequency that is optimized for receipt of charging power (e.g., 6.8 MHz).

Also as described above, since the implantable coil 332, and thus resonant tank circuit 350 are used for both data communication and to receive charging power, issues could arise if the resonant tank circuit 350 operates at an improper resonant frequency and these issues may be particularly problematic when the cochlear implant 300 is initialized/started (i.e., when the cochlear implant 300 is first powered and the resonant tank circuit 350 receives RF signals). Therefore, the cochlear implant 300 is configured such that when the cochlear implant initiates operation with an external device via an inductive link, the resonant tank circuit 350 is automatically initially tuned to the first resonant frequency that is optimized for data communications. At a subsequent time, the resonant tank circuit 350 may be adjusted so as to shift the resonant frequency to a second resonant frequency that is optimized for transfer of charging power to the cochlear implant 300.

This adjustment in the resonant frequency is caused by selectively opening/closing the RF tuning switch 368. When the RF tuning switch 368 is open (i.e., non-conducting), the resonant tank circuit 350 includes both capacitor 366 and capacitor 364 connected in series. As such, the resonant frequency of the resonant tank circuit 350 is controlled by the inductance of the implantable coil 332 (i.e., the value of $L_2$) and the capacitance associated with both capacitors 366 and 364 in series. However, when the RF tuning switch 368 is closed, the capacitor 364 is electrically shorted and the resonant frequency of the resonant tank circuit 350 is controlled by the inductance of the implantable coil 332 (i.e., the value of $L_2$) and the capacitance associated with capacitor 366 only.

Therefore, selectively opening/closing the RF tuning switch 368 alters one or more of the inductive or capacitive part of the resonant circuit 350 to change the resonant frequency thereof. When the RF tuning switch 368 is open, the resonant tank circuit 350 is optimized for receiving charging power (e.g., the resonant tank circuit resonates at approximately 6.78 MHz). When the RF tuning switch 368 is closed, the resonant tank circuit 350 is optimized for data communication (e.g., the resonant tank circuit resonates at approximately 5 MHz).

When the cochlear implant 300 initiates operation with an external device via an inductive link, the RF tuning switch 368 is always forced closed (conducting) so that only capacitor is connected to the implantable coil 332 (i.e., capacitor 364 is electrically shorted). As a result, the cochlear implant 300 is configured such that the resonant tank circuit 350 has a default resonant frequency of 5 MHz (i.e., a resonant frequency that is optimized for receiving data and/or operating power).

The RF tuning switch 368 is a MOSFET $M_1$ and, as described further below, the RF tuning switch 368 is forced closed by driving the gate 369 of the MOSFET $M_1$ with the rectified voltage of the implantable coil 332 (i.e., an output generated from the received radio frequency signals). More specifically, a current is induced in the implantable coil 332 when there is a magnetic field crossing through the implantable coil. The induced current in the implantable coil 332 creates a resonant tank voltage that is rectified by a diode 370 (diode $D_1$). That is, the cochlear implant 300 includes a diode 370 that, in response to the induced current in the implantable coil 332, generates a rectified tank voltage at 371. This rectified tank voltage is shown in FIG. 3 as $V_{DD\_PAR}$, which is used to drive the RF tuning switch 368 (i.e., to drive gate 368 of the MOSFET $M_1$). The RF tuning switch 368 is an inverter such that when there is a sufficiently high voltage at gate 369 (i.e., when $V_{DD\_PAR}$ exceeds a predetermined threshold so as to create a minimum gate-to-source voltage differential), the RF tuning switch 368 will be closed. The RF tuning switch 368 is configured such that even a small H-field crossing through the implant coil will close the switch. That is, the predetermined threshold at which $V_{DD\_PAR}$ will close the switch occurs even when the implantable coil 332 receives small magnetic fields. Therefore, when the cochlear implant of FIG. 3 initiates operation, and when the implantable coil 332 detects substantially any magnetic field, the rectified tank voltage (i.e., the rectified voltage of resonant tank circuit 350) will cause the RF tuning switch 368 to automatically close and tune the resonant frequency of the resonant tank circuit 350 to the first resonant frequency that is optimized for data communication and, potentially, for receiving operating power.

As detailed above with reference to FIG. 2, automatically initially tuning the resonant tank circuit 350 to a resonant frequency that is optimized for data communications (e.g., 5 MHz) ensures that the cochlear implant 300 has the ability to conduct data communications (e.g., bidirectional data communication) with an external data device (e.g., data device 105 of FIG. 1). In addition, the use of the rectified tank voltage, rather than a control component such as implant controller 326, as the mechanism to automatically tune the resonant tank circuit 350 to the first frequency eliminates the situation in which the implant controller 326 is unable to properly operate and/or actuate the switch (e.g., when no internal power is available).

Since the resonant tank circuit 350 is automatically initially tuned to a resonant frequency that is optimized for data communications (e.g., 5 MHz), the cochlear implant is able to conduct a bidirectional communication exchange with an external device that confirms whether or not charging of the battery 330 is authorized. If the charging is permitted, then implant controller 326 can switch/adjust the tuning of the resonant tank circuit 350 to the second resonant frequency (e.g., 6.78 MHz) that is optimized for receipt of the charging power (e.g., 6.78 MHz) by opening the RF tuning switch 368 and, accordingly, capacitor 364 in series with capacitor 366. Stated differently, once charging is desired, the implant controller 326 pulls/forces the gate 369 of the MOSFET $M_1$ to ground via a Schottky diode 377 (diode $D_3$), thereby causing the switch to open (i.e., become non-conducting).

As noted elsewhere herein, in certain arrangements, the 5 MHz resonant frequency supports a combined/modulated power data transfer (e.g., OOK) or a separated and interleaved power and data transfer (e.g., TDMA) between the cochlear implant 300 and the external device. That is, 5 MHz resonant frequency enables the bidirectional data communication link and meanwhile powering the active electronics of the implant, such as implant controller 326, at this same frequency so that the implant controller 326 may receive sufficient power so as to open the RF tuning switch 368 and adjust the resonant frequency of the resonant tank circuit 350.

Figure 4:
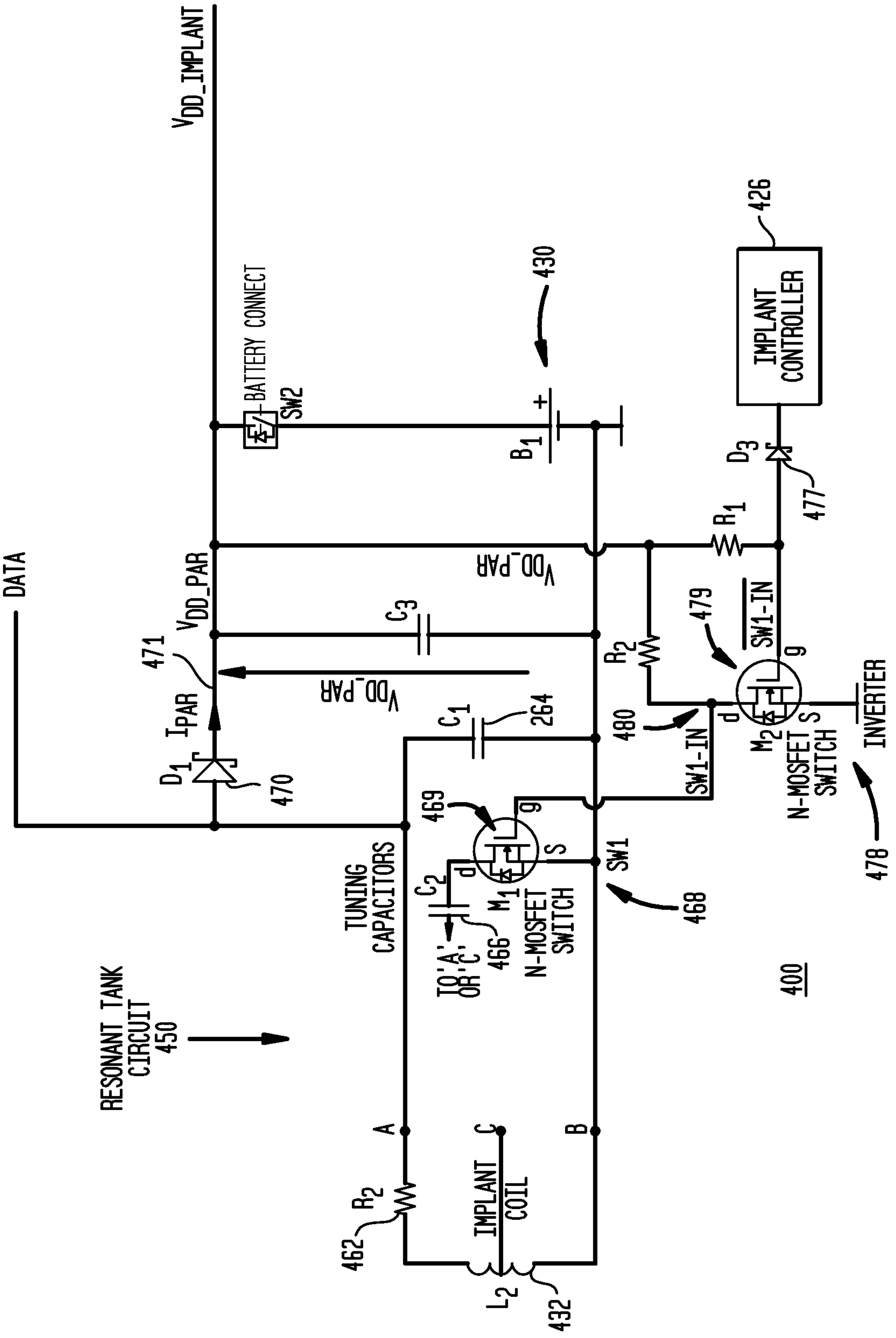
FIG. 4 is a schematic diagram illustrating a portion of a cochlear implant, in accordance with embodiments presented herein.
Figure 5:
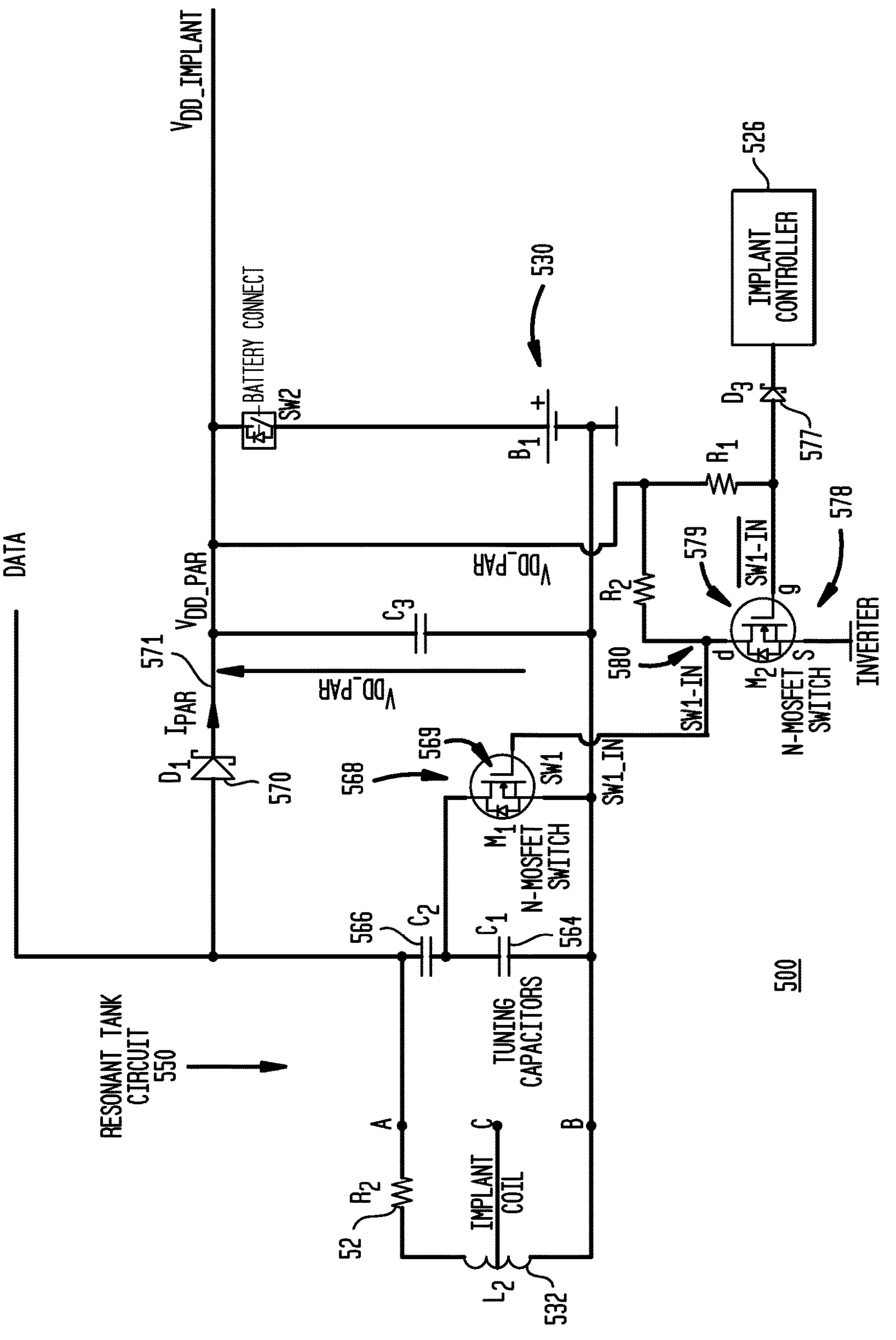
FIG. 5 is a schematic diagram illustrating a portion of a cochlear implant, in accordance with embodiments presented herein.

As noted above, FIGS. 2 and 3 illustrate resonant tank circuits 250 and 350, respectively, which are automatically initially tuned to a first resonant frequency that is optimized for data communications (i.e., the resonant tank circuits 250 and 350 are always forced to begin operating at the first resonant frequency that is optimized for data communications). At a subsequent time, the resonant tank circuits 250 and 350 may be adjusted so as to shift the resonant frequency to a second resonant frequency that is optimized for transfer of charging power to the cochlear implant. In the specific arrangements of FIGS. 2 and 3, the first resonant frequency is lower than the second frequency. That is, when the implant controllers determine that charging power should be transferred, the resonant tank circuits 250 and 350 are adjusted so as to shift the resonant frequency upward (i.e., tune to a higher frequency). It is to be appreciated that an upward resonant frequency shift is illustrative and that other arrangements may utilize a downward shift in the resonant frequency. FIGS. 4 and 5 illustrate examples arrangements configured to provide a downward shift in the resonant frequency to facilitate the transfer of charging power.

Referring first to FIG. 4, shown is a portion of a cochlear implant 400 that includes, among other elements, an implant controller 426, a rechargeable battery 430, an implant resonant tank circuit 450, a RF tuning switch 468, and a driver switch 478. The resonant tank circuit 450 is formed by at least an implantable coil 432, which is represented in FIG. 4 by an inductor $L_2$, a resistor 462 (resistor $R_2$), a capacitor 464 (capacitor $C_1$), and, at certain times, a capacitor 466 (capacitor $C_2$). The capacitor 466 is connected between the implantable coil 432 (e.g., at points 'A' or 'C' in FIG. 4) and the RF tuning switch 468. In the example of FIG. 4, the RF tuning switch 468, as well as its driver switch 478, are N-channel MOSFETs sometimes referred to herein as MOSFET $M_1$ and MOSFET $M_2$, respectively.

The rechargeable battery 430 is configured to store the energy needed to power the other elements of the cochlear implant 400, as well as to provide the current needed to electrically stimulate the recipient's cochlea, for at least a period of time. Similar to the above arrangements, the implantable coil 432 and the resonant tank circuit 450 are used for data communication with an external device (e.g., external data device 105), as well as for receiving charging power from an external charger (e.g., external charger 103). That is, the resonant tank circuit 450 is configured to operate at a first resonant frequency that is optimized for data communications (e.g., 15 MHz) and a second frequency that is optimized for receipt of charging power (e.g., 13.56 MHz).

Also as described above, since the implantable coil 432 and the resonant tank circuit 450 are used for data communication, issues could arise if the resonant tank circuit 450 operates at an improper resonant frequency and these issues may be particularly problematic when the cochlear implant 400 is initialized/started (i.e., when the cochlear implant 400 is first powered on and the resonant tank circuit 450 begins receiving radio frequency signals). Therefore, the cochlear implant 400 is configured such that, when the cochlear implant initiates operation with an external device via an inductive link, the resonant tank circuit 450 is automatically initially tuned to the first resonant frequency that is optimized for data communications. At a subsequent time, the resonant tank circuit 450 may be adjusted so as to shift the resonant frequency to a second resonant frequency that is optimized for transfer of charging power to the cochlear implant 400.

This adjustment in the resonant frequency is caused by selectively opening/closing the RF tuning switch 468. When the RF tuning switch 468 is open (i.e., non-conducting), only capacitor 464 is connected in parallel with the implantable coil 432 and the resonant frequency of the resonant tank circuit 450 is controlled by the inductance of the implantable coil 432 (i.e., the value of $L_2$) and the capacitance associated with capacitor 464. However, when the RF tuning switch 468 is closed, capacitor 466 is added in parallel with capacitor 464 and the resonant frequency of the resonant tank circuit 450 is controlled by the inductance of the implantable coil 432 (i.e., the value of $L_2$) and the parallel capacitance associated with capacitors 464 and 466. In the example of FIG. 4, when the RF tuning switch 468 is open, the resonant tank circuit 450 is optimized for data communications (e.g., the resonant tank circuit resonates at approximately 15 MHz). When the RF tuning switch 468 is closed, the resonant tank circuit 450 is optimized for receiving charging power (e.g., the resonant tank circuit resonates at approximately 13.56 MHz).

When the cochlear implant 400 initiates operation with an external device via an inductive link, the RF tuning switch 468 is always forced open (non-conducting) so that only capacitor 464 is connected to the implantable coil 432. As a result, the cochlear implant 400 is configured such that the resonant tank circuit 450 has a default higher resonant frequency of 15 MHz (i.e., a resonant frequency that is optimized for receiving data and/or operating power).

The RF tuning switch 468 is a MOSFET $M_1$ and, as described further below, the RF tuning switch 468 is forced open by pulling the gate 469 of the MOSFET $M_1$ to ground. More specifically, a current is induced in the implantable coil 432 when there is a magnetic field crossing through the implantable coil. The induced current in the implantable coil 432 creates a resonant tank voltage that is rectified by a diode 470 (diode $D_1$). That is, the cochlear implant 400 includes a diode 470 that, in response to the induced current in the implantable coil 432, generates a rectified tank voltage at 471. This rectified tank voltage is shown in FIG. 4 as $V_{DD\_PAR}$, which is used to drive the driver switch 478 (i.e., drive gate 479 of the MOSFET $M_2$). The driver switch 478 is an inverter such that it is closed (i.e., MOSFET $M_2$ starts to conduct) once the rectified voltage reaches a threshold voltage (i.e., when $V_{DD\_PAR}$ exceeds a predetermined threshold so as to create a minimum gate-to-source voltage differential). When this occurs, the voltage on the drain (d) 480 of MOSFET $M_2$ is pulled to ground, which in turn pulls the gate (g) 469 of MOSFET $M_1$ to ground. The RF tuning switch 468 is open when the voltage at gate 469 is below a predetermined threshold, and closed when the voltage at gate 469 exceeds the predetermined threshold. Therefore, when the gate 469 of the MOSFET $M_1$ is pulled to ground, the RF tuning switch 468 is open (i.e., MOSFET $M_1$ is non-conducting) because the gate voltage is below the predetermined threshold. In general, MOSFET $M_2$ can be viewed as a voltage inverter with its gate as an input and its drain as an output.

The RF tuning switch 478 is configured such that even low H-field lines crossing through the implant coil will close the switch and pull the gate 469 of MOSFET $M_1$ to ground. That is, the predetermined threshold at which $V_{DD\_PAR}$ will close the RF tuning switch 478 occurs even when the implantable coil 432 receives low magnetic fields. Therefore, when the implantable coil 432 detects substantially any magnetic field, independent of the operative frequency or tuned resonant tank circuit frequency, the rectified tank voltage (i.e., the rectified voltage of resonant tank circuit 450) will cause the driver switch 478 to automatically close, and RF tuning switch 468 to automatically open, thereby tuning the resonant frequency of the resonant tank circuit 450 to the first resonant frequency that is optimized for receiving data and/or operating power.

Similar to the above arrangements, automatically initially tuning the resonant tank circuit 450 to a resonant frequency that is optimized for data communications (e.g., 15 MHz) ensures that the cochlear implant 400 has the ability to conduct data communications (e.g., bidirectional data communication) with an external data device (e.g., data device 105 of FIG. 1). In addition, the use of the rectified tank voltage, rather than a control component such as implant controller 426, as the mechanism to automatically tune the resonant tank circuit 450 to the first frequency eliminates the situation in which the implant controller 426 is unable to properly operate and/or actuate the switch (e.g., when no internal power is available).

Since the resonant tank circuit 450 is automatically initially tuned to a resonant frequency that is optimized for data communications (e.g., 15 MHz), the cochlear implant 400 is able to conduct a bidirectional communication exchange with an external device that confirms whether or not charging of the battery 430 is authorized. If the charging is permitted, then implant controller 426 can switch/adjust the tuning of the resonant tank circuit 450 to the second resonant frequency that is optimized for receipt of the charging power (e.g., 13.56 MHz) by opening the RF tuning switch 478 and, accordingly, closing RF tuning switch 468. More particularly, implant controller 426 pulls the gate 479 of MOSFET $M_2$ to voltage ground via a Schottky diode 477 (diode $D_3$). As a result, MOSFET $M_2$ is non-conducting and the gate voltage of MOSFET $M_1$ rises above the threshold voltage causing MOSFET $M_1$ to begin conducting (i.e., switch 468 closes). As noted, when the RF tuning switch 468 is closed, capacitor 466 is added in parallel to capacitor 464 and the resonant frequency of the resonant tank circuit 450 falls/lowers to the second resonant tank frequency that can be used to recharge battery 430.

As noted elsewhere herein, in certain arrangements, the 15 MHz resonant frequency supports a combined/modulated power data transfer (e.g., OOK) or a separated and interleaved power and data transfer (e.g., TDMA) between the cochlear implant 400 and the external device. That is, the 15 MHz resonant frequency enables the bidirectional data communication link and meanwhile powering the active electronics of the implant, such as implant controller 426, at this same frequency so that the implant controller 426 may receive sufficient power so as to close the RF tuning switch 468 and adjust the resonant frequency of the resonant tank circuit 450.

Referring next to FIG. 5, shown is a portion of a cochlear implant 500 that includes, among other elements, an implant controller 526, a rechargeable battery 530, an implant resonant tank circuit 550, an RF tuning switch 568, and a driver switch 578. The resonant tank circuit 550 is formed by at least an implantable coil 532, which is represented in FIG. 5 by an inductor $L_2$, a resistor 562 (resistor $R_2$), a capacitor 566 (capacitor $C_2$), and, at certain times, a capacitor 564 (capacitor $C_1$). The capacitors 564 and 566 are connected in series with one another and the RF tuning switch 568 is connected in parallel with the capacitor 564. In the example of FIG. 5, the RF tuning switch 568, as well as its driver switch 578, are N-channel MOSFETs sometimes referred to herein as MOSFET $M_1$ and MOSFET $M_2$, respectively.

The rechargeable battery 530 is configured to store the energy needed to power the other elements of the cochlear implant 500, as well as to provide the current needed to electrically stimulate the recipient's cochlea, for at least a period of time. Similar to the above arrangements, the implantable coil 532 and the resonant tank circuit 550 are used for data communication with an external device (e.g., external data device 105), as well as for receiving charging power from an external charger (e.g., external charger 103). That is, the resonant tank circuit 550 is configured to operate at a first resonant frequency that is optimized for data communications (e.g., 15 MHz) and a second frequency that is optimized for receipt of charging power (e.g., 13.56 MHz).

Also as described above, since the implantable coil 532 and the resonant tank circuit 550 are used for data communication and for receiving charging power, issues could arise if the resonant tank circuit 550 operates at an improper resonant frequency and these issues may be particularly problematic when the cochlear implant 500 is initialized/started (i.e., when the cochlear implant 500 is first powered on). Therefore, the cochlear implant 500 is configured such that, when the cochlear implant initiates operation with an external device via an inductive link, the resonant tank circuit 550 is automatically initially tuned to the first resonant frequency that is optimized for data communications. At a subsequent time, the resonant tank circuit 550 may be adjusted so as to shift the resonant frequency to a second resonant frequency that is optimized for transfer of charging power to the cochlear implant 500.

This adjustment in the resonant frequency is caused by selectively opening/closing the RF tuning switch 568. When the RF tuning switch 568 is open (i.e., non-conducting), the resonant tank circuit 550 includes both capacitor 566 and capacitor 564 connected in series and the resonant frequency of the resonant tank circuit 550 is controlled by the inductance of the implantable coil 532 (i.e., the value of $L_2$) and the capacitance associated with both capacitors 566 and 564 in series. However, when the RF tuning switch 568 is closed, the capacitor 564 is electrically shorted and the resonant frequency of the resonant tank circuit 550 is controlled by the inductance of the implantable coil 532 (i.e., the value of $L_2$) and the capacitance associated with capacitor 566 only. In the example of FIG. 5, when the RF tuning switch 568 is open, the resonant tank circuit 550 is optimized for receiving data and/or operating power (e.g., the resonant tank circuit resonates at approximately 15 MHz). When the RF tuning switch 568 is closed, the resonant tank circuit 550 is optimized for receiving charging power (e.g., the resonant tank circuit resonates at approximately 13.56 MHz).

When the cochlear implant 500 initiates operation with an external device via an inductive link, the RF tuning switch 568 is always forced open (non-conducting) so that both capacitor 564 and capacitor 566 are connected to the implantable coil 532. As a result, the cochlear implant 500 is configured such that the resonant tank circuit 550 has a default higher resonant frequency of 15 MHz (i.e., a resonant frequency that is optimized for receiving data and/or operating power).

The RF tuning switch 568 is a MOSFET $M_1$ and, as described further below, the RF tuning switch 568 is forced open by pulling the gate 569 of the MOSFET $M_1$ to ground. More specifically, a current is induced in the implantable coil 532 when there is a magnetic field crossing through the implantable coil. The induced current in the implantable coil 532 creates a resonant tank voltage that is rectified by a diode 570 (diode $D_1$). That is, the cochlear implant 500 includes a diode 570 that, in response to the induced current in the implantable coil 532, generates a rectified tank voltage at 571. This rectified tank voltage is shown in FIG. 5 as $V_{DD\_PAR}$, which is used to drive the driver switch 578 (i.e., drive gate 579 of the MOSFET $M_2$). The RF driver switch 578 is an inverter such that it is closed (i.e., MOSFET $M_2$ starts to conduct) once the rectified voltage reaches a threshold voltage (i.e., when $V_{DD\_PAR}$ exceeds a predetermined threshold). When this occurs, the voltage on the drain (d) 580 of MOSFET $M_2$ is pulled to ground, which in turn pulls the gate (g) 569 of MOSFET $M_1$ to ground. The RF tuning switch 568 is open when the voltage at gate 569 is below a predetermined threshold, and closed when the voltage at gate 569 exceeds the predetermined threshold. Therefore, when the gate 569 of the MOSFET $M_1$ is pulled to ground, the RF tuning switch 568 is open (i.e., MOSFET $M_1$ is non-conducting) because the gate voltage is below the predetermined threshold. In general, MOSFET $M_2$ can be viewed as a voltage inverter with its gate as an input and its drain as an output.

The RF tuning switch 578 is configured such that even low H-field lines crossing through the implant coil will close the switch and pull the gate 569 of MOSFET $M_1$ to ground. That is, the predetermined threshold at which $V_{DD\_PAR}$ will close the RF tuning switch 578 occurs even when the implantable coil 532 receives low magnetic fields. Therefore, when the cochlear implant of FIG. 5 initiates operation, and when the implantable coil 532 detects substantially any magnetic field, independent of the operative frequency or tuned resonant tank circuit frequency, the rectified tank voltage (i.e., the rectified voltage of resonant tank circuit 550) will cause the driver switch 578 to automatically close, and RF tuning switch 568 to automatically open, thereby tuning the resonant frequency of the resonant tank circuit 550 to the first resonant frequency that is optimized for receiving data and/or operating power.

Similar to the above arrangements, automatically tuning the resonant tank circuit 550 to a resonant frequency that is optimized for data communications (e.g., 15 MHz) ensures that the cochlear implant 500 has the ability to conduct data communications (e.g., bidirectional data communication) with an external data device (e.g., data device 105 of FIG. 1). In addition, the use of the rectified tank voltage, rather than a control component such as implant controller 526, as the mechanism to automatically tune the resonant tank circuit 550 to the first frequency eliminates the situation in which the implant controller 526 is unable to properly operate and/or actuate the switch (e.g., when no internal power is available).

Since the resonant tank circuit 550 is automatically tuned to a resonant frequency that is optimized for data communications (e.g., 15 MHz), the cochlear implant 500 is able to conduct a bidirectional communication exchange with an external device that confirms whether or not charging of the battery 530 is authorized. If the charging is permitted, then implant controller 526 can force switch the tuning of the resonant tank circuit 550 to the second resonant frequency that is optimized for receipt of the charging power (e.g., 13.56 MHz) by opening the driver switch 578 and, accordingly, closing RF tuning switch 568. More particularly, implant controller 526 pulls the gate 579 of MOSFET $M_2$ to voltage ground via a Schottky diode 577 (diode $D_3$). As a result, MOSFET $M_2$ is non-conducting and the gate voltage of MOSFET $M_1$ rises above the threshold voltage causing MOSFET $M_1$ to begin conducting (i.e., switch 568 closes). As noted, when the RF tuning switch 568 is closed, only capacitor 566 is connected to the implantable coil 532 (i.e., capacitor 564 is electrically shorted or bypassed) and the resonant frequency of the resonant tank circuit 550 falls/lowers to the second resonant tank frequency that can be used to recharge battery 530.

As noted elsewhere herein, in certain arrangements, the 15 MHz resonant frequency supports a combined/modulated power data transfer (e.g., OOK) or a separated and interleaved power and data transfer (e.g., TDMA) between the cochlear implant 500 and the external device. That is, the 15 MHz resonant frequency enables the bidirectional data communication link and meanwhile powering the active electronics of the implant, such as implant controller 526, at this same frequency so that the implant controller 526 may receive sufficient power so as to close the RF tuning switch 568 and adjust the resonant frequency of the resonant tank circuit 550.

FIGS. 2, 3, 4, and 5 each illustrate examples in which one or more RF tuning and/or driver switches are configured to be selectively actuated so as to adjust the capacitance of the corresponding resonant tank circuit. That is, in each of these examples, the one or more RF tuning switches are opened/closed to add or remove capacitors from the corresponding resonant tank circuits. It is to be appreciated that embodiments presented herein may use one or more RF tuning switches to also or alternatively adjust the inductance of the corresponding resonant tank circuit. For example, in alternative embodiments, the one or more RF tuning switches may be opened/closed to add or remove inductors from the corresponding resonant tank circuit.

Figure 6:
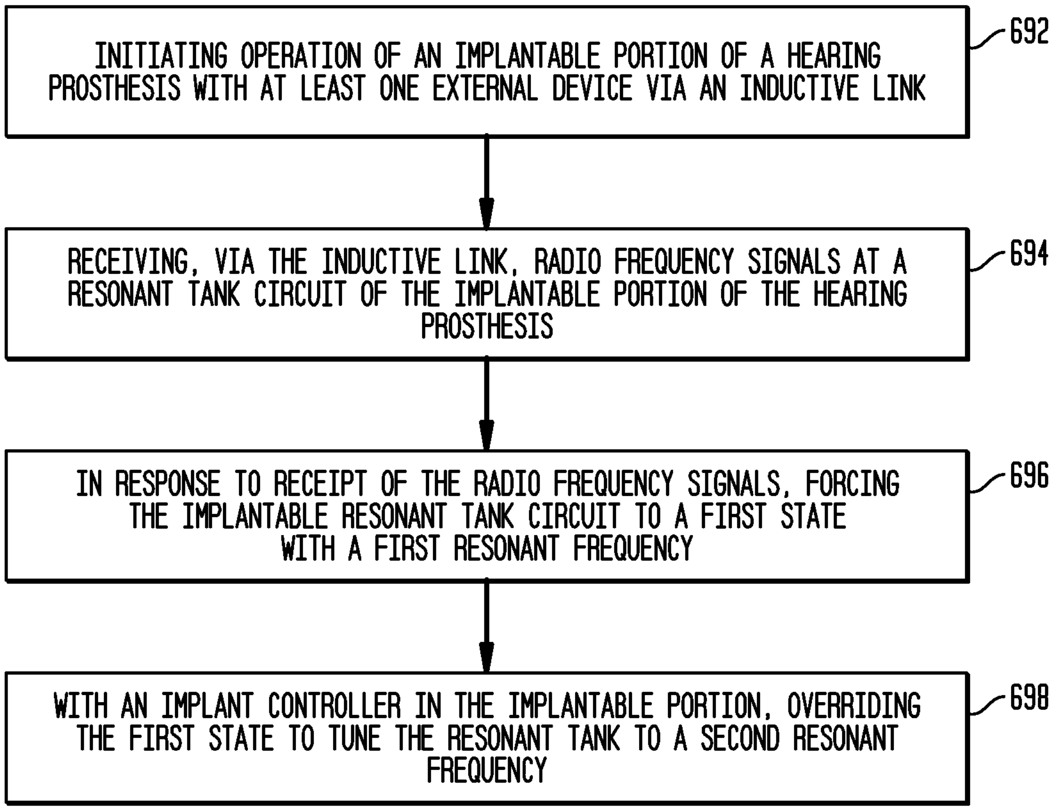
FIG. 6 is a flowchart of a method, in accordance with embodiments presented herein.

FIG. 6 is a flowchart of a method 690 in accordance with embodiments presented herein. Method 690 begins at 692 where an implantable portion of a hearing prosthesis initiates operation with one or more external device via an inductive link (e.g., a closely-coupled inductive link). At 694, radio frequency signals are received by the resonant tank circuit in the implantable portion of the hearing prosthesis receives, via the inductive link. At 696, in response to receipt of the radio frequency signals, the implantable resonant tank circuit is forced to a first state with a first resonant frequency (e.g., by rectifying a voltage of the resonant tank circuit, where the voltage is generated in response to receipt of the radio frequency signals). At 698, an implant controller in the implantable portion overrides the first state to tune the resonant tank to a second resonant frequency that is optimized for receiving charging power.

Although embodiments have been primarily described with reference to cochlear implants, it is to be appreciated that the techniques presented herein may be implemented in other implantable medical devices, such as other types of auditory prostheses.

It is to be appreciated that the embodiments presented herein are not mutually exclusive.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. An implantable component, comprising:

a resonant circuit including an implantable coil and at least one switch, wherein the implantable coil is configured to be inductively coupled with an external device such that the external device generates a magnetic field at the implantable coil; and wherein at least upon initiating operation of the implantable component with the external device, a rectified voltage generated by the magnetic field present at the implantable coil directly drives the at least one switch so as to automatically initially force tune the resonant circuit to a first frequency that enables a data exchange with the external device via the implantable coil.

2. The implantable component of claim 1, further comprising:

an implant controller connected to the at least one switch and configured to subsequently selectively activate the at least one switch to override the initial force tuning of the resonant circuit to the first frequency such that the resonant circuit is selectively tuned to a second frequency.

3. The implantable component of claim 2, further comprising:

a rechargeable battery, wherein the second frequency is a frequency that configures the resonant circuit to receive charging power via the implantable coil when recharging the rechargeable battery, and wherein the first frequency is different from the second frequency.

4. The implantable component of claim 2, further comprising:

an implantable microphone; and a sound processor, wherein the sound processor is configured to use signals from the implantable microphone as a primary sound input when receiving charging power at the second frequency, and to use signals from the external device as the primary sound input when receiving operating power and data signals operative at the first frequency.

5. The implantable component of claim 2, further comprising:

a rechargeable battery, wherein the implant controller is configured to use the data exchange at the first frequency to authorize recharging of the rechargeable battery, and only after authorizing the recharging of the rechargeable battery, activate the at least one switch to tune the resonant circuit to the second frequency to receive charging power via the implantable coil.

6. The implantable component of claim 2, wherein the implantable component is configured to:

receive, via the implantable coil, a data signal from the external device operative at the first frequency, authenticate the external device based on the received data signal, and after authenticating the external device, switch the resonant circuit to the second frequency to receive charging power via the implantable coil.

7. The implantable component of claim 2, wherein the first frequency is optimized to concurrently receive operating power and data at the implantable coil, and wherein the second frequency is optimized to receive charging power at the implantable coil.

8. The implantable component of claim 2, wherein the at least one switch is configured to be selectively actuated by the implant controller so as to adjust one or more of the inductance or capacitance of the resonant circuit to tune the resonant circuit to the second frequency.

9. The implantable component of claim 1, wherein upon initial coupling of the implantable coil with an external coil of the external device, the rectified voltage present at the implantable coils is used to directly drive the at least one switch to a closed configuration to force tune the resonant circuit to the first frequency.

10. The implantable component of claim 1, wherein upon initial coupling of the implantable coil with an external coil of the external device, the rectified voltage present at the implantable coils is used to directly drive the at least one switch to an open configuration to force tune the resonant circuit to the first frequency.

11. The implantable component of claim 1, wherein the resonant circuit is configured to receive data and operating power from a modulated carrier signal operative at the first frequency.

12. The implantable component of claim 1, wherein the resonant circuit is configured to receive interleaved operating power and data signals operative at the first frequency.

13. The implantable component of claim 1, further comprising:

a stimulation circuit, and wherein the implantable component is configured to use operating power received from the external device via the implantable coil operative at the first frequency to power the stimulation circuit.

14. A method, comprising:

initiating operation of an implantable component of a medical device with an external device, wherein the external device includes an external coil that emits a magnetic field;

generating, in response to receiving the magnetic field, a rectified voltage at an implantable coil of a resonant circuit of the implantable component, wherein the resonant circuit comprises the implantable coil and at least one switch;

in response to initiating operation of the implantable component with the external device external coil, driving the least one switch directly with the rectified voltage generated at the implantable coil to initially automatically detune the resonant circuit to resonate at a first frequency; and enabling a data exchange with the external device via the implantable coil.

15. The method of claim 14, wherein driving the least one switch with the rectified voltage comprises:

applying the rectified voltage received at the resonant circuit to at least one node of the at least one switch to directly drive the at least one switch to a closed configuration to automatically detune the resonant circuit to the first frequency.

16. The method of claim 14, wherein driving the least one switch with the rectified voltage comprises:

applying the rectified voltage received at the resonant circuit to at least one node of the at least one switch to directly drive the at least one switch to an open configuration to automatically detune the resonant circuit to the first frequency.

17. The method of claim 14 further comprising:

with an implant controller in the implantable component, subsequently selectively activating the at least one switch to selectively tune the resonant circuit to resonate at a second frequency that is different from the first frequency.

18. The method of claim 17, wherein the implantable component of the medical device comprises a rechargeable battery, and wherein the first frequency is optimized to concurrently exchange data with the external device and to receive operating power from the external device, while the second frequency is optimized to receive charging power for charging the rechargeable battery.

19. The method of claim 18, further comprising:

while the resonant circuit is tuned to the first frequency, exchanging data with the external device to authorize recharging of the rechargeable battery; and only after authorizing the recharging of the rechargeable battery, selectively activating the at least one switch with the implant controller to tune the resonant circuit to resonate at the second frequency to receive the charging power.

20. The method of claim 14, wherein the resonant circuit is configured to receive interleaved operating power and data signals operative at the first frequency.

* * * * *